(12) United States Patent
Doerr et al.

(10) Patent No.: US 8,886,305 B2
(45) Date of Patent: Nov. 11, 2014

(54) VENTRICULAR HEART STIMULATOR (75) Inventors: Thomas Doerr, Berlin (DE); Frank Tscherch, Bestensee (DE); Ulrich Tietze, Berlin (DE)

(73) Assignee: Biotronik CRM Patent AG, Baar (CH)

( * ) Notice: Subject to any disclaimer, the term of this patent is extended or adjusted under 35 U.S.C. 154(b) by 1274 days.

(21) Appl. No.: 12/407,703

(22) Filed: Mar. 19, 2009

(65) Prior Publication Data
US 2009/0264946 A1 Oct. 22, 2009

(30) Foreign Application Priority Data
Apr. 22, 2008 (DE) .................. 10 2008 020 123

(51) Int. Cl.
*A61N 1/05* (2006.01)
*A61N 1/39* (2006.01)
*A61N 1/362* (2006.01)
*A61N 1/368* (2006.01)
*A61N 1/37* (2006.01)

(52) U.S. Cl.
CPC ............ *A61N 1/3925* (2013.01); *A61N 1/3622* (2013.01); *A61N 1/368* (2013.01); *A61N 1/3704* (2013.01); *A61N 1/3962* (2013.01); *A61N 1/3682* (2013.01); *A61N 1/3684* (2013.01)
USPC ................................. 607/5; 607/4

(58) Field of Classification Search
USPC ........................................ 607/4, 5
See application file for complete search history.

(56) References Cited

U.S. PATENT DOCUMENTS

| | | | | |
|---|---|---|---|---|
| 5,193,550 A | * | 3/1993 | Duffin | 600/510 |
| 5,814,089 A | * | 9/1998 | Stokes et al. | 607/32 |
| 5,853,426 A | | 12/1998 | Shieh | |
| 5,857,977 A | | 1/1999 | Caswell et al. | |
| 6,112,116 A | | 8/2000 | Fischell et al. | |
| 6,558,098 B1 | | 5/2003 | Angehrn et al. | |
| 7,149,569 B1 | | 12/2006 | Fain | |
| 7,349,732 B1 | | 3/2008 | Kil et al. | |

FOREIGN PATENT DOCUMENTS

| | | |
|---|---|---|
| EP | 0 202 748 | 11/1986 |
| EP | 0 308 536 | 3/1989 |
| FR | 2 524 808 | 10/1983 |
| WO | WO 92/09331 | 6/1992 |

OTHER PUBLICATIONS

European Search Report, dated Jul. 2, 2009.
(Continued)

*Primary Examiner* — Alyssa M Alter
(74) *Attorney, Agent, or Firm* — ARC IP Law, PC; Joseph J. Mayo (57) ABSTRACT

The invention relates to an implantable ventricular heart stimulator (10), comprising an at least partially electrically conductive housing (12), an electrode line terminal for connection of a ventricular defibrillation electrode line (20) and a terminal for a defibrillation electrode (26). According to the invention, the heart stimulator has a far-field electrocardiogram detection unit (70) which has a first input connected to the terminal for the ventricular defibrillation electrode and has a second input connected to the electrically conductive housing and designed or configured to generate a far-field electrocardiogram on the basis of the electric potentials applied to the two inputs during operation. The inventive heart stimulator also has a far-field electrocardiogram evaluation unit (72) which is connected to the far-field electrocardiogram detection unit and is designed to detect signal features characteristic of atrial depolarizations in a far-field electrocardiogram generated by the far-field electrocardiogram detection unit.

19 Claims, 9 Drawing Sheets (56) References Cited

OTHER PUBLICATIONS

Greenhut et al. "Detectin of atrial activation by interaventricular electrogram morphology analysis: a study to determine the feasibility of P wave synchronous pacing from a standard ventricular lead" Pace-Pacing and Clinical Electrophysiology, Blacwell Futura Publishing, Malden MA, Bd. 16, No. 6, Mar. 1, 1993.
International Search Reoprt dated Mar. 25, 1992 for PCT Application No. PCT/US 91/08269, 2 pages.
German Search Report, dated Dec. 8, 2008.

* cited by examiner

VENTRICULAR HEART STIMULATOR

This application takes priority from German Patent Application DE 10 2008 020 123.5, filed 22 Apr. 2008, the specification of which is hereby incorporated herein by reference.

BACKGROUND OF THE INVENTION

1. Field of the Invention

The invention relates to an implantable ventricular heart stimulator for stimulating the right or left or both ventricles of the heart. Such a heart stimulator is known as a single-chamber heart stimulator or as a biventricular heart stimulator and may also include the function of an implantable cardioverter/defibrillator (ICD).

2. Description of the Related Art

Implantable heart stimulators in the form of heart pacemakers or cardioverter/defibrillators are fundamentally known. Such heart stimulators are usually connected to electrode lines which have stimulation electrodes or defibrillation electrodes in one ventricle of the heart or in the immediate proximity thereof. A heart pacemaker may deliver an electric stimulation pulse to the myocardium of a heart chamber via a stimulation electrode to thereby induce a stimulated ventricular contraction if the stimulation pulse is of a sufficient intensity and if the myocardial tissue is not just then in a refractory phase. To trigger a stimulated ventricular contraction in this way, electrode lines having relatively small-area stimulation electrodes are usually used because for triggering a stimulated ventricular contraction, it is sufficient if only a small portion of the myocardium of this ventricle is stimulated initially. Within the context of this description, such a stimulated ventricular contraction is referred to as a stimulated event. If a natural ventricular contraction occurs, this is referred to as intrinsic action or an intrinsic event within the context of this description. A contraction of the right atrium of the heart, for example, is known as an atrial event, which may be a natural atrial event or, in the case of an atrial pacemaker, a stimulated atrial event. In the same sense, natural (intrinsic) and stimulated left ventricular and right ventricular events may also be differentiated.

With regard to the stimulation of a heart chamber, in particular the right or left ventricle of the heart, it should also be pointed out that the stimulation is performed in synchronization with the atrium in order to reproduce as well as possible the natural contractile frequency of the heart in which the right atrium contracts first and then, after an atrioventricular conduction time, the right ventricle contracts, while at the same time or slightly later the left ventricle contracts. Under certain circumstances, the natural ventricular contraction subsequent to a natural contraction of the atrium fails to occur. In typical biventricular pacemakers, the natural contraction of the atrium is therefore detected as an intrinsic atrial event and the right and/or left ventricle is/are stimulated after a predefined conduction time.

Such natural (intrinsic) events are detected by deriving electric potentials of the myocardial of the respective ventricle with the help of sensing electrodes, which are part of a corresponding electrode line. The sensing electrodes may at the same time be stimulation electrodes and may be used alternately as stimulation electrodes and as sensing electrodes. Typically an electrode pair consisting of a tip electrode and a ring electrode is provided for sensing, the tip electrode also serving as a stimulation electrode. The sensing and stimulation in the ventricle are performed with the help of a ventricular electrode line and the stimulation and sensing in the atrium (in the right atrium) are performed using an atrial electrode line which is separately connected in the respective heart stimulator. In addition, a left ventricular electrode line may also be provided, typically passing through the coronary sinus and a lateral vein branching off therefrom into proximity to the left ventricle and may have a small-area stimulation electrode and/or sensing electrode there.

The typical stimulation modes which are implementable with a heart stimulator may be assumed to be known (VVD, DDD, etc.) so they need not be explained further here.

Beyond the properties of a heart pacemaker already described here, of delivering to the heart a stronger current pulse, which should not only stimulate (depolarize) a small portion of the myocardium but should depolarize the largest possible amount of myocardium and thus make it refractory to thereby interrupt the typical cycling stimulation of the myocardium that is typical of fibrillation. Such a pulse is known as a defibrillation shock. It is typically delivered via a large-area defibrillation electrode in comparison with the stimulation electrode or sensing electrode.

This is often implemented in the form of a shock coil on the outer surface of the electrode line in the respective chamber of the heart. For example, a ventricular electrode line in addition to a tip electrode or a ring electrode for stimulation and sensing may also have a ventricular shock coil as well as a proximal shock coil situated in the superior vena cava after implantation.

A defibrillation shock is usually delivered when the heart stimulator detects a fibrillation, i.e., an irregular high-frequency intrinsic activity of the heart which does not lead to complete contraction of the respective chamber of the heart. Such a fibrillation is classified as a tachycardiac arrhythmia, which includes tachycardias in addition to fibrillations. In contrast with fibrillation, complete contraction of the respective chamber of the heart occurs regularly in tachycardia but at a higher rate than would be physiologically appropriate. Such tachycardias can often be treated by antitachycardiac stimulation and do not require a defibrillation shock. Fibrillations are usually treated with a defibrillation shock.

In ventricular tachycardias, a distinction is made between supraventricular tachycardias (SVT) and ventricular tachycardias (VT) in the narrower sense. The latter originate in the ventricle itself, whereas supraventricular tachycardias originate in the atrium. For the treatment initiated after detection of tachycardia, the type of ventricular tachycardia (ventricular tachycardia in the narrower sense (VT) or supraventricular tachycardia (SVT)) is important.

BRIEF SUMMARY OF THE INVENTION

The problem on which the present invention is based is that atrial synchronous stimulation of the ventricle or discrimination (also differentiation) between supraventricular tachycardias (SVT) and ventricular tachycardias (VT) presupposes detection of natural atrial events. In the state of the art, this is done with the help of atrial electrode lines which have corresponding sensing electrodes. The corresponding options for treatment and detection are thus opened up for other heart stimulators, which are not or cannot be connected to such an atrial electrode line.

The object of the present invention is to also develop detection options and treatments which presuppose detection of atrial events for stimulators which are not or cannot be connected to an atrial electrode line because a corresponding electrode line terminal is not provided in the heart stimulator, for example.

According to the invention, this object is achieved by an implantable heart stimulator having a housing with an electrically conductive surface at least partially and a defibrillation electrode line terminal for connection of a ventricular defibrillation electrode line, such that the defibrillation electrode line terminal has an electric contact connected to a mating contact, which is in turn electrically connected to the defibrillation electrode in the case of a defibrillation electrode line connected to the heart stimulator. In addition, the inventive heart stimulator has a far-field electrocardiogram detection unit, which has a first input connected to the terminal for the ventricular defibrillation electrode and a second input connected to the electrically conductive surface of the housing of the heart stimulator. The far-field electrocardiogram detection unit is designed to generate a far-field electrocardiogram on the basis of the electric potentials applied to the two inputs during operation. Furthermore, the inventive heart stimulator has a far-field electrocardiogram evaluation unit connected to the far-field electrocardiogram detection unit and designed to detect signal features in a far-field electrocardiogram generated by the far-field electrocardiogram detection unit, these features being characteristic of atrial depolarization. Atrial depolarization characterizes atrial intrinsic actions or intrinsic (natural) atrial events. Such an implantable heart stimulator may also detect atrial events without contact with a sensing electrode in the atrium of the heart, thereby opening up possibilities for detection and treatment based on detection of atrial events.

The heart stimulator preferably has as the ventricular heart stimulator a ventricular stimulation unit connected to a left ventricular or right ventricular stimulation electrode. As already explained in the introduction, such a stimulation electrode is an electrode having a much smaller surface area than the defibrillation electrode which is used to record the far-field electrocardiogram. Such a ventricular stimulation electrode is, for example, a tip electrode on a ventricular electrode line but also a ring electrode on a ventricular electrode line. The ventricular stimulation unit is also designed to generate and deliver ventricular stimulation pulses. To do so, it may be connected to a stimulation control unit which controls the ventricular stimulation unit.

Likewise, the implantable heart pacemaker may also have a ventricular sensing unit which is connected or can be connected to a ventricular sensing electrode via a ventricular electrode line that is connected or can be connected. The ventricular sensing electrode, like the ventricular stimulation electrode, is a small-area electrode in comparison with the defibrillation electrode. The ventricular sensing electrode may also be formed by an electrode pair, e.g., a ventricular ring electrode and a ventricular tip electrode, of which the ventricular tip electrode, for example, may also be a stimulation electrode at the same time. The ventricular sensing unit is designed to receive and evaluate electric potentials of the myocardium via the ventricular sensing electrode and, for example, to detect intrinsic ventricular events by comparing the electric potentials recorded by the ventricular sensing unit with a threshold value. If the electric potential exceeds the threshold value, then a ventricular event is detected. The detection may also be based on the analysis of a filtered potential curve in which randomly high potentials due to noise are filtered out. The detection of ventricular events with the help of a ventricular sensing electrode is basically known.

According to a preferred embodiment variant of the heart stimulator, it has a defibrillation electrode line terminal suitable for connection of a ventricular defibrillation electrode line having two shock coils namely a proximal shock coil (e.g., provided for arrangement in the superior vena cava) and a distal shock coil. The heart stimulator is designed so that the two shock coils are to be joined to the far-field electrocardiogram detection unit independently of one another. This detection unit is preferably designed to be connected to the proximal shock coil of the two available shock coils in order to determine the far-field electrocardiogram from the potential difference between the proximal shock coil and the electrically conductive surface area of the heart stimulator housing.

According to an alternative embodiment variant, the heart stimulator may also be designed so that the far-field electrocardiogram detection unit may be connected optionally to a proximal shock coil or a distal shock coil of a ventricular defibrillation electrode line.

The far-field electrocardiogram evaluation unit is preferably designed to detect sensing events in the far-field electrocardiogram by comparison with a fixed, predefined or variable threshold value.

To detect atrial events as sensing event in the far-field electrocardiogram in a targeted manner, the far-field electrocardiogram evaluation unit is preferably designed to detect such sensing events in the form of signal peaks of the far-field electrocardiogram, which are not to be assigned to an intrinsic atrial event and which remove the signal peaks detected in this way from the far-field electrocardiogram. The far-field electrocardiogram evaluation unit is then also designed to further process the far-field electrocardiogram thereby obtained for detection of atrial sensing events. These atrial sensing events may then in turn be detected by threshold value comparison from the far-field electrocardiogram from which the other signal peaks are eliminated.

Typical signal peaks in the far-field electrocardiogram that are not to be assigned to intrinsic atrial events include signal peaks which are traced back to ventricular events. Accordingly, the far-field electrocardiogram evaluation unit is preferably connected to the ventricular sensing unit and is designed to assign ventricular events detected by the ventricular sensing unit to corresponding signal peaks in the far-field electrocardiogram in order to determine the signal peaks, which are traced back to ventricular events. The far-field electrocardiogram evaluation unit is then designed to remove such signal peaks from the far-field electrocardiogram.

Additionally or alternatively, the far-field electrocardiogram evaluation unit may also be designed to detect signal sections of the far-field electrocardiogram to be assigned to ventricular events by signal shape analysis (morphology analysis) in order to then remove the corresponding signal sections from the far-field electrocardiogram. It is especially effective, although more complex, if the far-field electrocardiogram evaluation unit is designed to base the assignment of signal components of the far-field electrocardiogram on ventricular events based on a morphological analysis and on the detection signal originating from the ventricular sensing unit.

As already mentioned, the signals for atrial events obtained without a dedicated atrial sensing electrode in the manner described above may be used to control the heart stimulator. It is especially advantageous if the heart stimulator is designed to process the atrial sensing signal obtained by detection of atrial sensing events, so that unnecessary ventricular stimulation is avoided. In this regard it may be advantageous to have a time delay in the sensing events detected in the far-field electrocardiogram before further processing in order to implement in this way a hysteresis function which is known with traditional atrial synchronous heart pacemakers.

It is likewise advantageous if atrial sensing signals are used in a left ventricular or biventricular heart stimulator to control a cardiac resynchronization therapy (CRT) including AV time optimization. According to another preferred embodiment, the heart stimulator is designed to perform a cardiac resynchronization therapy, preferably including AV time optimization.

As already mentioned, detection of atrial events is also beneficial in conjunction with the detection and treatment of tachycardias and fibrillations. In a preferred embodiment variant, the heart stimulator is therefore an implantable cardioverter/defibrillator (ICD) designed to detect ventricular events and to assign them to a tachycardia or a fibrillation, if necessary, depending on the heart rate (and/or period). This is done, for example, by comparing the interval between two successive ventricular sensing events or the inverse thereof, namely the heart rate with a threshold value. If the interval, optionally averaged over multiple cycles, is smaller than a predefined threshold value or if the optionally averaged heart rate is higher than a predefined threshold value, the ICD detects a fibrillation. If the heart rate and/or interval between successive ventricular events is within a range which is not yet assigned to a ventricular fibrillation but represents a physiologically inappropriately high heart rate (this range is also known as the VT zone), then the heart stimulator preferably detects a ventricular tachycardia. For example, a first limit rate or a first limit interval may be provided, which serves as a reference value for differentiating between regular heart rates and tachycardias and a second higher limit rate and/or a second shorter limit interval, which serves as a reference value for differentiating between tachycardias and fibrillations.

Such a heart stimulator is preferably designed so that its far-field electrocardiogram evaluation unit detects atrial events only when the analysis of the ventricular events described previously have shown that there is no ventricular fibrillation but instead there is only a ventricular tachycardia.

In addition, the stimulator is preferably designed to perform a discrimination between supraventricular tachycardia (SVT) and ventricular tachycardia (VT) on atrial events detected with the help of the far-field electrocardiogram evaluation unit by evaluating the occurrence of ventricular events in a simultaneous comparison of the occurrence of atrial events. In particular, the heart stimulator may be designed to trigger an antitachycardiac stimulation after detecting a ventricular tachycardia. If this antitachycardiac stimulation influences the chronological occurrence of atrial events, then the heart stimulator detects a ventricular tachycardia (VT), otherwise it detects a supraventricular tachycardia (SVT), as described in the parallel pending German patent application (our ref. 08.004).

In addition, a heart stimulator designed to perform an atrial synchronous stimulation or electrotherapy depending on detection of atrial events is also preferred if the far-field electrocardiogram evaluation unit detects atrial sensing events in the far-field electrocardiogram and otherwise switches to a single-chamber operating mode that does not rely on detection of atrial events. Such single-chamber operating modes for ventricular stimulation (e.g., a VVI mode) or detection and discrimination of ventricular tachycardias are fundamentally known. A single-chamber operating mode for discrimination of ventricular tachycardias has the effect that the heart stimulator assigns ventricular tachycardias that are associated with a regular heart rate to a supraventricular tachycardia (SVT) and assigns ventricular tachycardias that are associated with a comparatively variable rapid heart rate to an actual ventricular tachycardia (VT).

Additional advantageous embodiments of an inventive heart stimulator are derived from combinations, although not mentioned explicitly here, of the various advantageous features of such a heart pacemaker that are described here.

BRIEF DESCRIPTION OF THE DRAWINGS

The invention will now be explained in greater detail on the basis of an exemplary embodiment with respect to the figures, in which.

DETAILED DESCRIPTION OF THE INVENTION

Figure 1:
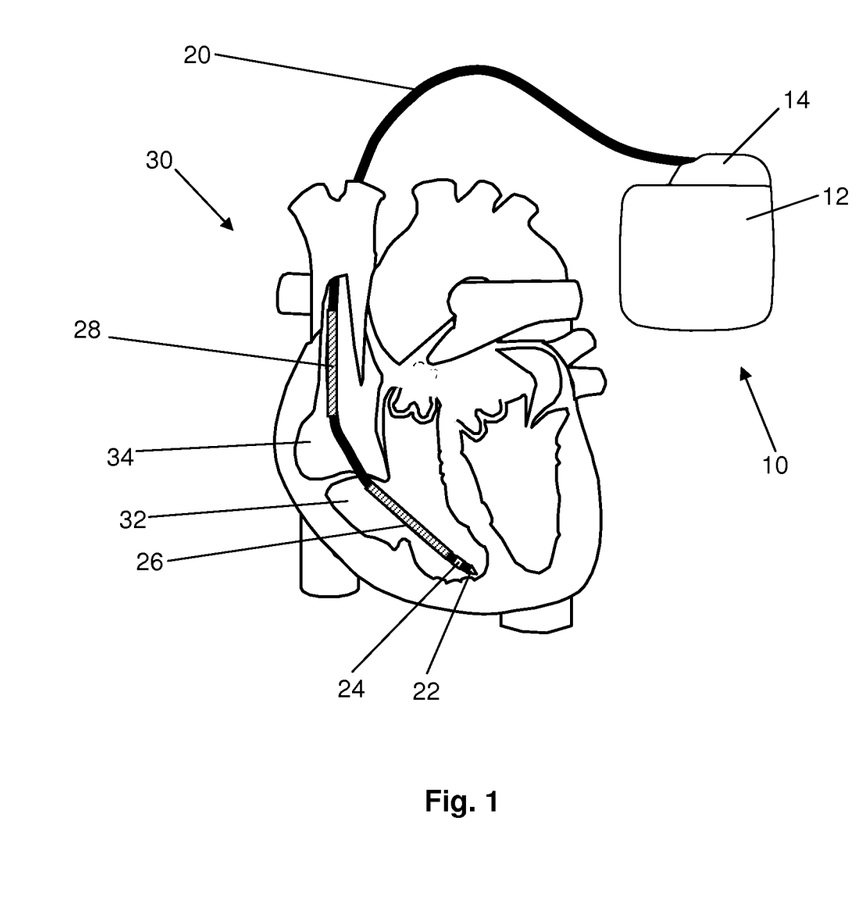
FIG. 1: shows a heart stimulator in the form of an implantable single-chamber cardioverter/defibrillator in combination with electrode lines connected thereto.

FIG. 1 shows a ventricular heart pacemaker 10 with a housing 12 and a header 14. The housing 12 is hollow and has at least partially an electrically conductive surface; typically the housing 12 is made of a biocompatible metal such as titanium. The housing 12 contains a battery and electronic components of the heart stimulator 10. The header 14 contains sockets, e.g., for an electrode line 20.

The electrode line 20 illustrated is a ventricular electrode line having a ventricular tip electrode 22 and a ventricular ring electrode 24. Of these, the ventricular tip electrode 22 serves as a stimulation electrode. The ventricular tip electrode 22 and the ventricular ring electrode 24 together form an electrode pair for bipolar sensing of ventricular events. For this purpose, the ventricular tip electrode 22 and the ventricular ring electrode 24 are connected to a ventricular stimulation unit and a ventricular sensing unit in the interior of the housing 12 of the heart stimulator 10 (details are described with reference to FIG. 2). Furthermore, the ventricular electrode line 20 has a ventricular shock coil 26 as a distal shock coil and a proximal shock coil 28. The ventricular shock coil 26 is arranged on the ventricular electrode line 20 in such a way that when it is inserted into a heart 30, it is situated in the ventricle 32 of the heart. The ventricular tip electrode 22 is then in the apex of the ventricle 32 of the heart 30. The proximal shock coil 28 is in the superior vena cava of the heart 30 when the ventricular electrode line 20 is implanted. No special electrode line is provided for stimulation of the right atrium 34 of the heart 30. Likewise there is no atrial sensing electrode. The heart stimulator 10 does not have any atrial electrode line at all, but nevertheless offers the functionality of heart stimulators that are connected to an atrial electrode line. This is explained in greater detail below.

Figure 2:
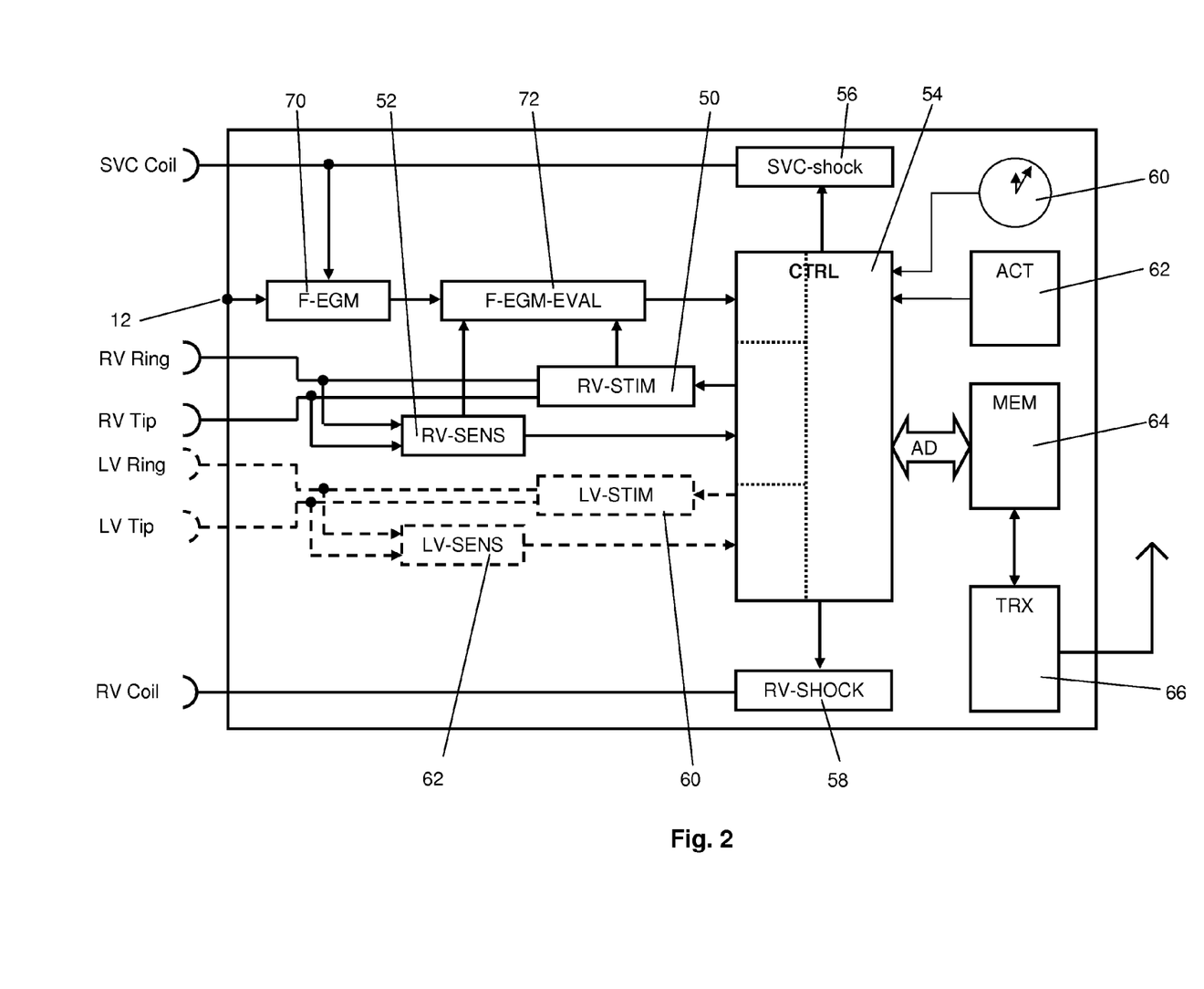
FIG. 2 shows a schematic block diagram of the heart stimulator from FIG. 1.

FIG. 2 shows in a schematic block diagram components of the heart stimulator 10 situated in the interior of the housing 12. This diagram is not necessarily conclusive. In particular, components shown with dashed lines in FIG. 2 are not implemented in the heart stimulator 10 from FIG. 1 but are implemented only in heart stimulators such as those illustrated in FIG. 6 or 7, for example.

As already indicated, the heart stimulator 10 has terminal contacts in its header 14 for connecting the corresponding mating contacts of an electrode line plug on the proximal end of the electrode line 20. These contacts provide the electric connection to the electrodes of the electrode line 20. For example, the proximal shock coil 28 is connected to the contact SVC coil; the ventricular (distal) shock coil 26 is connected to the terminal RV coil; the right ventricular tip electrode 22 is connected to the terminal RV tip and the right ventricular ring electrode is connected to the terminal RV ring. The right ventricular tip electrode 22 and the right ventricular ring electrode 24 are each connected to a right ventricular stimulation unit 50 and a right ventricular sensing unit 52 via the terminals RV tip and RV ring. The right ventricular sensing unit 52 is connected at the output to a stimulation control unit 54, which in turn has an output connected to the right ventricular stimulation unit 50. The right ventricular stimulation unit 50 is designed to generate a ventricular stimulation pulse in response to a corresponding control signal of the stimulation control unit 54 and to deliver it at least via the contact RV tip.

The functioning of the right ventricular sensing unit 52 is explained in greater detail below with reference to FIG. 3. The right ventricular sensing unit is fundamentally designed to evaluate the course of a signal derived from the difference between the potentials applied to the terminals RV tip and RV ring. This signal curve typically contains signal peaks which occur in the case of ventricular depolarization. Ventricular depolarization precedes contraction of the ventricular myocardium and thus characterizes ventricular sensing events. These may be detected from the signal curve by comparing the potentials with a threshold value, which is set so that the signal peaks associated with ventricular depolarization exceed the threshold value and the ventricular sensing unit 52 is able to detect ventricular sensing events by threshold value comparison when the threshold value is exceeded.

To generate and deliver defibrillation shocks, shock generators 56 and 58 are also provided, connected by the terminal SVC coil to the proximal shock coil 28 and/or by the terminal RV coil to the distal shock coil 26. The two defibrillation shock generators 56 and 58 are also connected to the stimulation control unit 54. Additional features of the heart stimulator 10 include a timer 60, which is used for interval measurement and heart rate determination, for example, and an activity sensor 62 designed to detect physical activity by a patient, e.g., by detection of motion, to make it possible for the stimulation control unit 54 to adjust the stimulation rate to the physiological needs of the patient. In addition, the heart stimulator 10 has a memory 64 for saving control parameters and physiological parameters which are obtained, for example, by evaluating the various signals picked up by the heart stimulator 10.

Finally, the heart stimulator 10 also has a telemetry unit 66 by which the heart stimulator 10 can wirelessly transmit physiological parameters obtained and saved to an external device or by which the heart stimulator 10 can receive control parameters which control the functioning of the heart stimulator 10.

In the sense of the present invention, the heart stimulator 10 also has a far-field electrocardiogram detection unit 70 connected at the input to the electrically conductive housing 12 of the heart stimulator 10 and connected at the other end to the terminal SVC coil for the proximal defibrillation electrode and/or shock coil 28. The potential difference between these two inputs then yields a far-field electrocardiogram, which is recorded by the far-field electrocardiogram detection unit 70, amplified and passed through analog-digital conversion and filtered, as explained in greater detail with reference to FIG. 3. The far-field electrocardiogram obtained and processed in this way is applied to an output of the far-field electrocardiogram detection unit 70. This output is connected to an input of a far-field electrocardiogram evaluation unit 72. This far-field electrocardiogram evaluation unit 72 also has one input connected to the right ventricular sensing unit 52 and another input connected to the right ventricular stimulation unit 50. As an alternative to this, a single input of the far-field electrocardiogram evaluation unit 72 may also be provided, this input being connected to the stimulation control unit 54. These additional inputs of the far-field electrocardiogram evaluation unit 72 serve to supply signals characterizing the ventricular sensing events and/or ventricular stimulation events to the far-field electrocardiogram evaluation unit 72. The far-field electrocardiogram evaluation unit is designed to evaluate the far-field electrocardiogram formed by the far-field electrocardiogram detection unit 70, taking into account signals characterizing ventricular sensing events and stimulation events in order to detect signal features which characterize atrial (sensing) events in the far-field electrocardiogram. This is also explained in greater detail below with reference to the following FIGS. 3 and 4.

Figure 3:
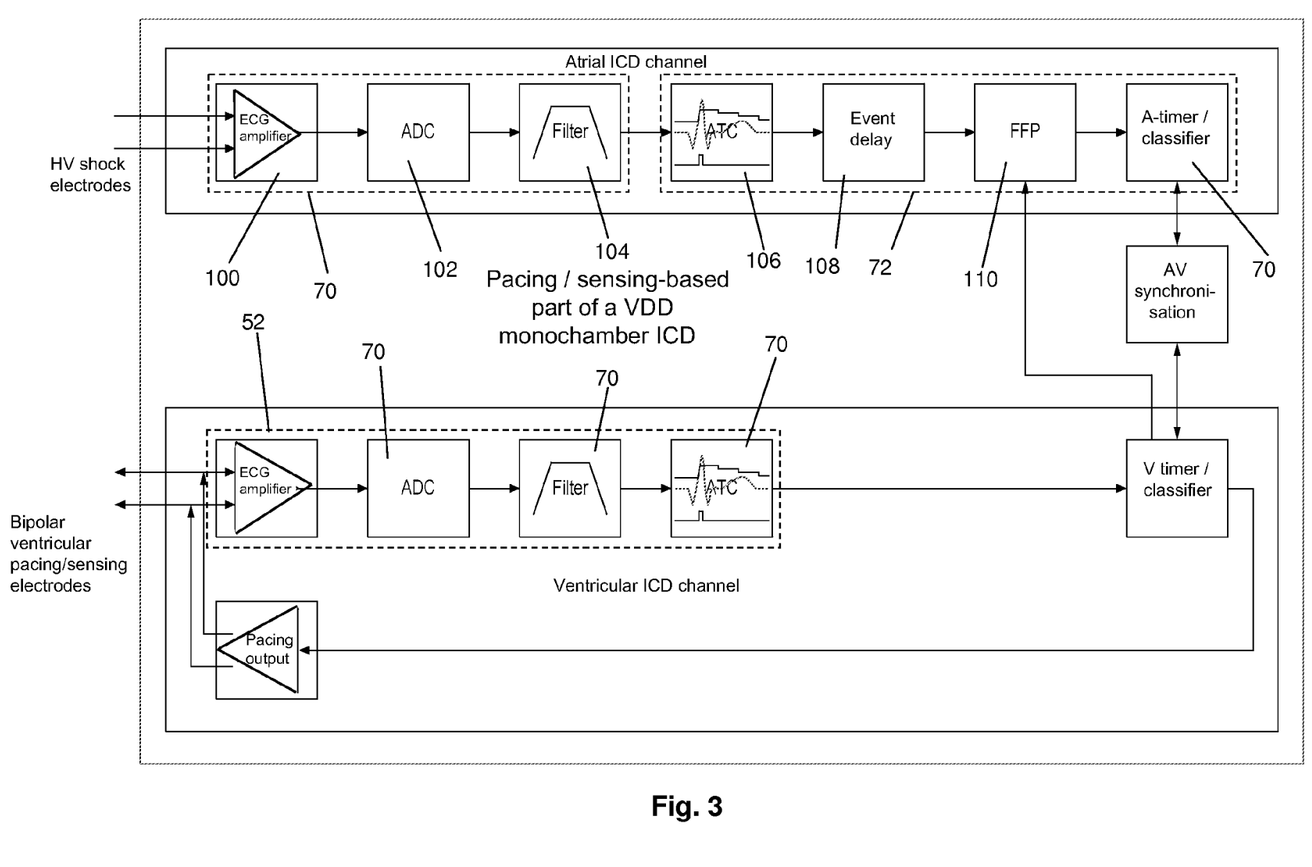
FIG. 3 shows a few components of the heart stimulator from FIGS. 1 and 2 in a detailed view.

Of these figures, FIG. 3 shows a few components of the far-field electrocardiogram detection unit 70 and the far-field electrocardiogram evaluation unit 72 on the one hand as well as the ventricular sensing unit 52 on the other hand in a detail diagram. It should be noted here that the combination of far-field electrocardiogram detection unit 70 and far-field electrocardiogram evaluation unit 72 in FIG. 3 is designated as an atrial ICD channel but there is no further differentiation between far-field electrocardiogram detection unit and far-field electrocardiogram evaluation unit.

The components of the atrial channel are explained below on the basis of their functioning. The far-field electrocardiogram signals derived from the defibrillation electrode 28 is sent to an analog-digital converter (ADC) 102 via a preamplifier 100 and is then digitally bandpass filtered through a digital bandpass filter 104. Then by continuous comparison with an algorithmically adjusted threshold value in a comparator 106, sensing events which are delayed in time by a delay member 108 and are further processed are obtained from the filtered signal. It is thus to be expected that the sensing events obtained in this way will indicate not only events relevant to atrial activity but also those to be assigned to ventricular activity. Therefore, in a subsequent far-field protection unit 110, any events that occur and are to be assigned to the ventricle are suppressed for further signal processing.

Figure 4:
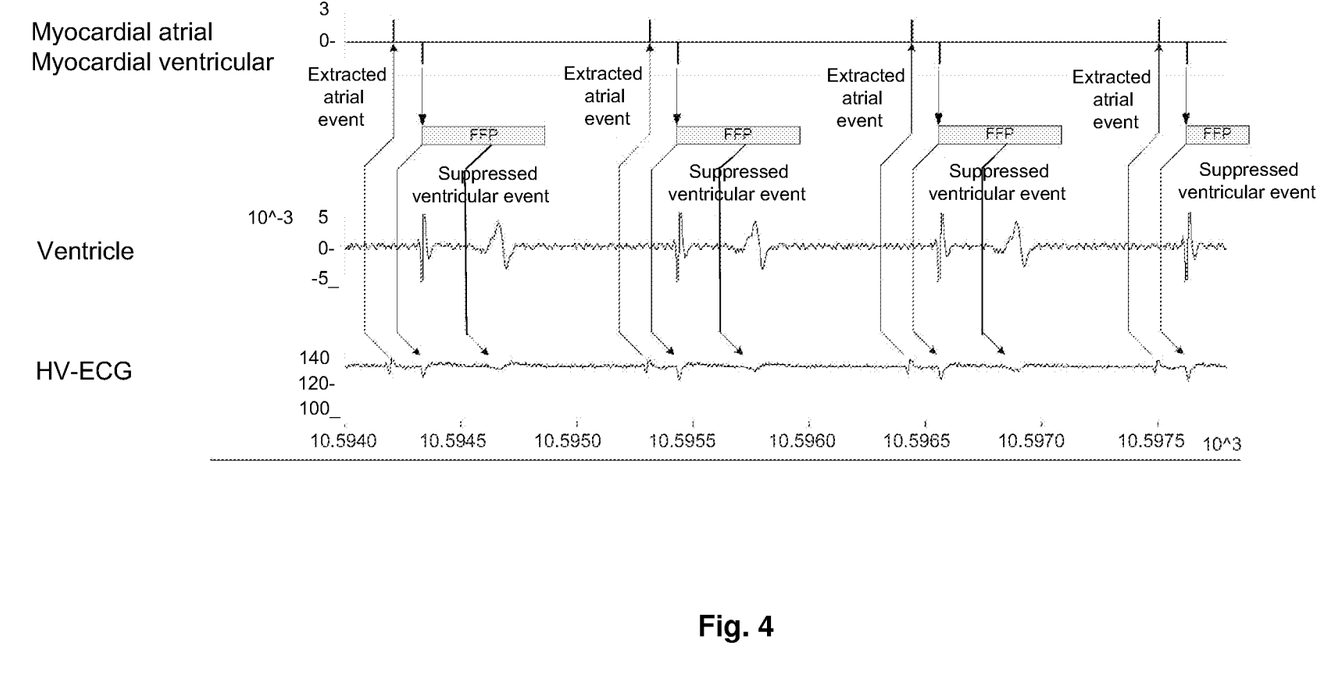
FIG. 4 shows a far-field electrocardiogram (below) obtained with the help of the implantable single-chamber cardioverter/defibrillator from FIGS. 1 and 2 together with an intraventricular electrocardiogram (center) and marker signals (above)

Their functioning is described in greater detail below with reference to FIG. 4. FIG. 4 shows as an example a section of a far-field electrocardiogram (bottom row) together with an intraventricular electrocardiogram (middle row) which was obtained as a bipolar electrocardiogram using the ventricular sensing electrodes 22 and 24 as well as with atrial and ventricular marker signals for the events evaluated in the atrial and ventricular channels. The intraventricular electrocardiogram was derived in the ventricle from the bipolar pacing/ sensing electrodes 22 and 24 localized there with the help of the components of the ventricular channel (i.e., the ventricular sensing unit) depicted at the bottom of FIG. 3.

With detection of a ventricular event by the ventricular sensing unit 52, the latter generates a ventricular marker signal as a ventricular sensing signal and delivers it to the far-field protection unit 110, which then, starting from the ventricular event, opens a time window (FFP) in which events which might occur in the atrial channel assigned to the far-field electrocardiogram are suppressed because they can be attributed causally to the ventricle, e.g., T-waves.

As a result, only atrial events extracted from the far-field electrocardiogram are available in the atrial channel for a synchronized ventricular stimulation control in VDD mode.

The atrial events obtained in this way are then acted upon by the delay element 108 with a positive AV time hysteresis and sent to the stimulation control unit 54, which then starts an AV interval (atrioventricular delay interval) in an essentially known manner, at the end of which a ventricular stimulation pulse is triggered if the ventricular sensing unit has not previously detected a ventricular event during the AV interval (demand mode, ventricular stimulation pulses are triggered only as needed). The AV time hysteresis introduced by the delay member causes ventricular stimulation pulses to be triggered only when no ventricular contractions occur within the AV interval even with a moderately delayed natural AV conduction. This function can be expanded by means of search and repeat functions and then corresponds to the current "IRS plus"/"I-OPT" function in known dual-chamber ICDs by the present applicant.

Figure 5:
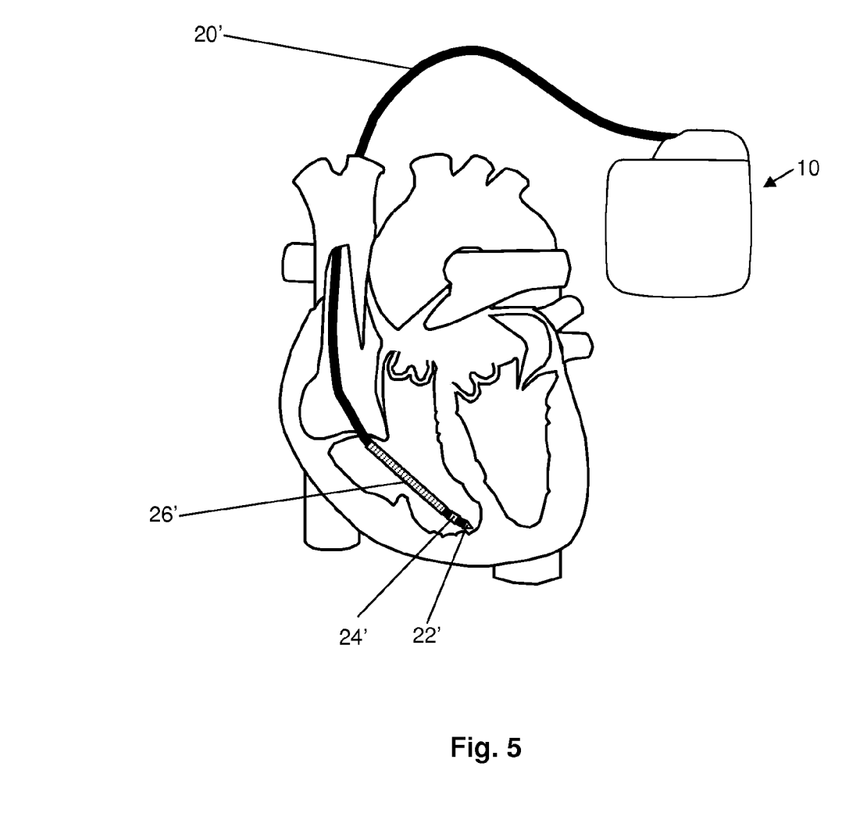
FIG. 5 shows an alternative implantable single-chamber cardioverter/defibrillator in combination with electrode lines connected thereto.

FIG. 5 shows a ventricular heart stimulator 10' like that in FIG. 1. However, in contrast with that one, the right ventricular electrode line 20' has only one shock coil 26' as a defibrillation electrode in the right ventricle. Accordingly, the far-field electrocardiogram detection unit with the heart stimulator 10' is also not connected to a shock coil in the superior vena cava but instead is connected to the right ventricular shock coil 26'. Otherwise the heart stimulators from FIGS. 1 and 5 are the same.

Figure 6:
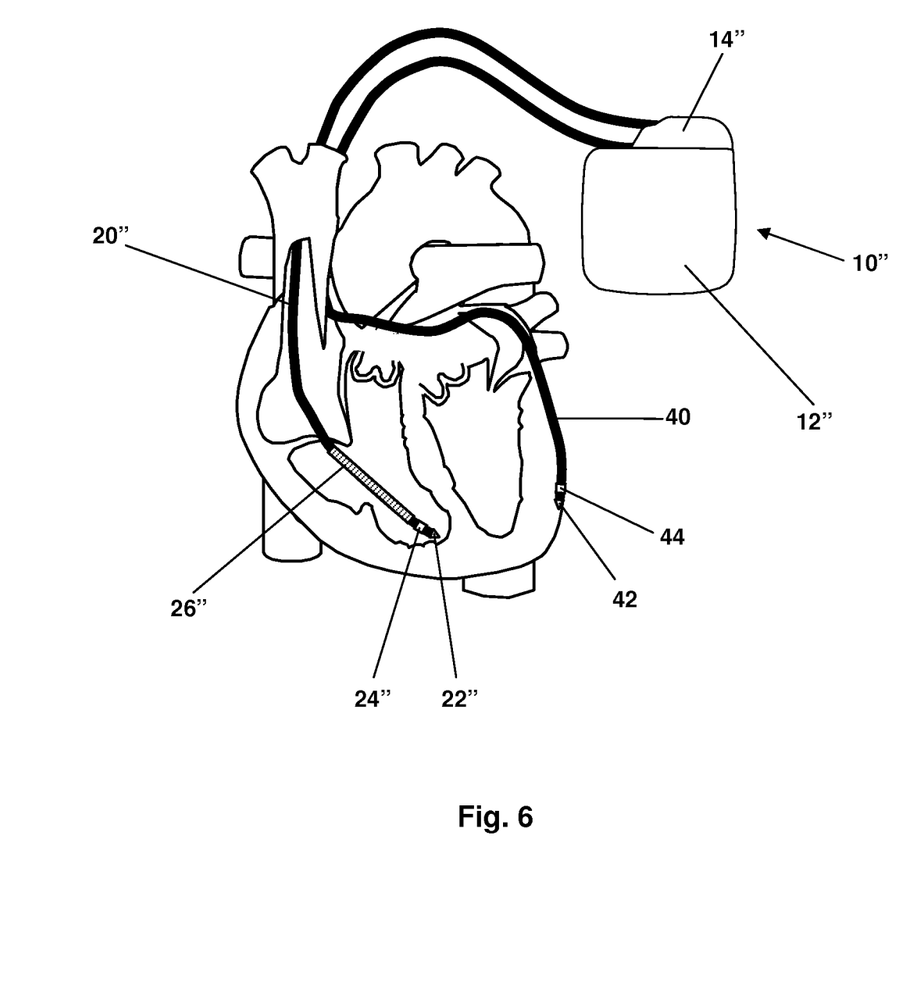
FIG. 6 shows an implantable biventricular cardioverter/defibrillator in combination with electrodes lines connected thereto.

As FIG. 6 shows, the inventive heart stimulator may also be embodied as a biventricular heart stimulator 10" also having a left ventricular electrode line 40 in addition to a right ventricular electrode line 20". In implantation, the left ventricular electrode line 20" is advanced through the coronary sinus into a lateral vein branching off from the former, so that its distal end is in the area of the left ventricular myocardium in the implanted state. At the distal end of the left ventricular electrode line 40, a left ventricular tip electrode 42 is attached as a relatively small-area stimulation and sensing electrode and at a small distance therefrom, a left ventricular ring electrode 44, which, as a stimulation and sensing electrode, is also a relatively small-area electrode.

As indicated with dashed lines in FIG. 2, the two left ventricular stimulation and sensing electrodes 42 and 44 are each connected to a left ventricular stimulation unit 60 and a left ventricular sensing unit 62.

Figure 7:
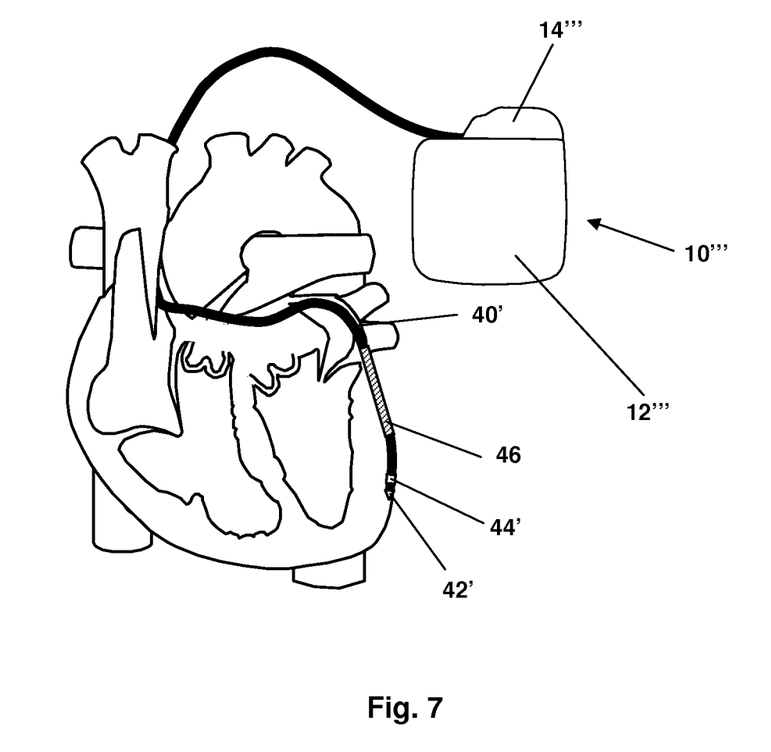
FIG. 7 shows an implantable left ventricular single-chamber cardioverter/defibrillator in combination with electrode lines connected thereto.

FIG. 7 shows that the inventive ventricular heart stimulator may also be designed as a strictly left ventricular heart stimulator 10'''. During operation, it is connected only to a left ventricular electrode line 40', which also has a left ventricular shock coil 46' as a relatively large-area defibrillation electrode in addition to having left ventricular tip electrode 42' and ring electrode 44' of the type already described in conjunction with FIG. 6 as a relatively large-area defibrillation electrodes. In the heart stimulator 10 in FIG. 7, the latter serves to derive the far-field electrocardiogram and is connected to the corresponding far-field electrocardiogram detection unit.

The heart stimulators from FIGS. 6 and 7 allow cardiac resynchronization therapy (CRT) without requiring an atrial electrode line. Instead, the atrial sensing signal determination is performed from a far-field electrocardiogram as described above. The heart stimulators 10" and 10''' from FIGS. 6 and 7 can use the atrial information thereby obtained, optionally combined with a negative AV time hysteresis, to control AV time-optimized resynchronization therapy (CRT therapy) through biventricular or left ventricular stimulation. The header 14" of the biventricular heart stimulator 10" in FIG. 6 therefore has two sockets according to the IS-1 standard for the connection of the stimulation and sensing electrodes and two socket according to the DF-1 standard for connection of the defibrillation electrodes.

As mentioned briefly, the invention may also be used with heart stimulators designed as implantable cardioverter/defibrillators (ICD). With these, the far-field electrocardiogram obtained as described above and the information derived from it can be used in an advantageous manner to discriminate between ventricular tachycardia (VT) and supraventricular tachycardia (SVT).

Figure 8:
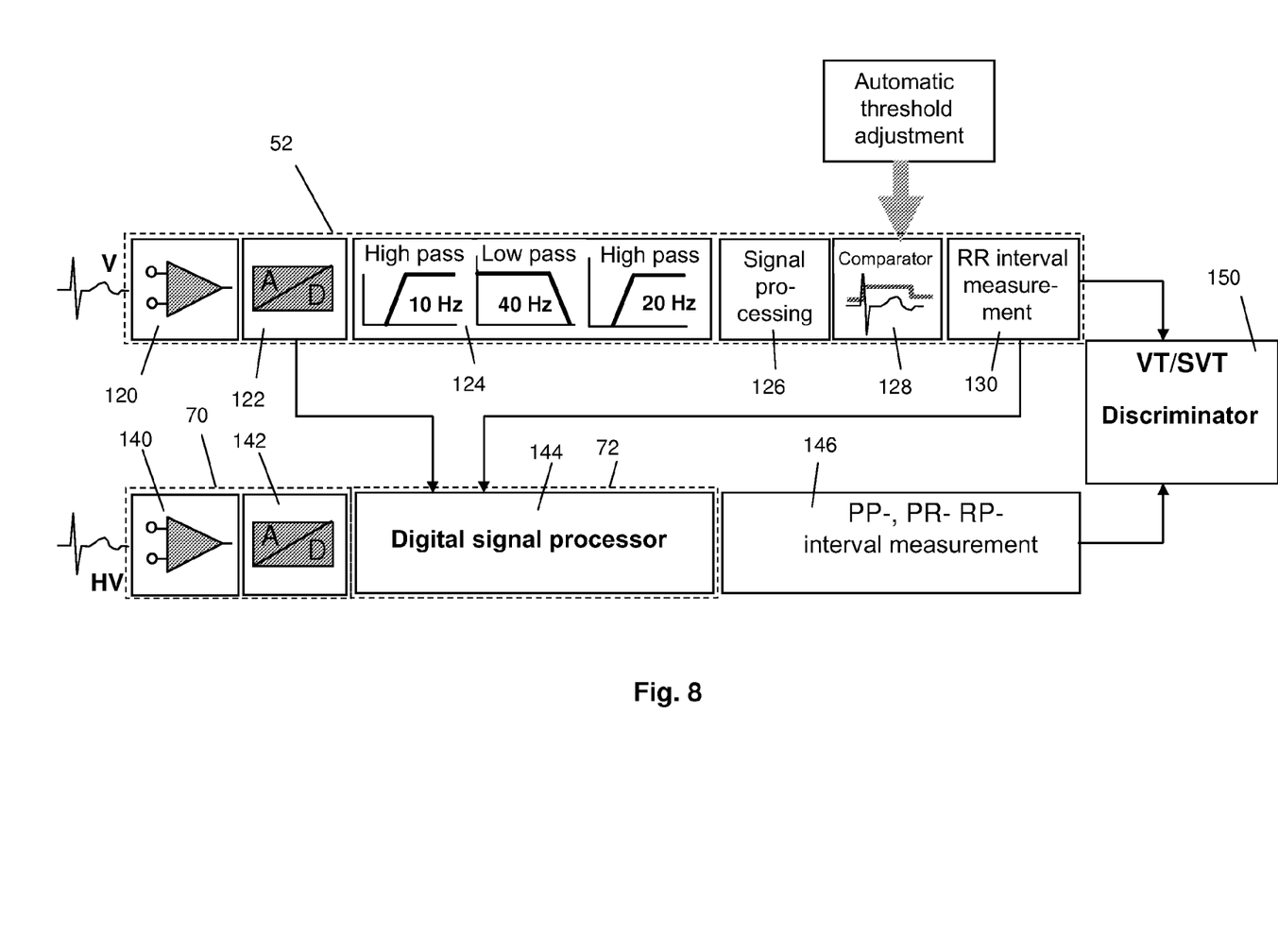
FIG. 8 shows a few components of the heart stimulator from FIG. 5 in a detailed view.

FIG. 8 shows a detail of a block diagram of the single-chamber ICD with a expanded VT/SVT discrimination to illustrate VT/SVT discrimination.

First an intraventricular electrocardiogram is recorded by the sensing electrode pair 22 and 24 and is first amplified by means of an amplifier 120, then digitized by means of an analog-digital converter 122 and finally digitally filtered through filter 124 in multiple stages. Next a signal processing unit 126 performs a rectification and, if necessary, an inversion of the intraventricular electrocardiogram signal, followed by determination of the sensing signal in a comparator stage 128, which determines R-waves as signal features typical of ventricular depolarization in the intraventricular electrocardiogram by means of automatically included threshold values. The R-waves are then sent to an RR interval measuring unit 130 for determination of the RR intervals, i.e., the intervals between successive ventricular events.

In a second atrial sensing channel, the far-field electrocardiogram derived between the proximal shock coil and the housing of the heart stimulator (HV) is first amplified by an amplifier 140 and digitized by means of an analog-digital converter 142. Next in a digital signal processor 144, the P-wave is extracted from the far-field electrocardiogram as a signal feature characteristic of atrial depolarization using the intraventricular electrocardiogram (source: 20) and is sent to a downstream PP interval measuring unit 146. The signal processing, which is highly power consuming under some circumstances in the digital signal processor, is performed only when the measured RR intervals, i.e., the intervals between successive ventricular events, are within a VT zone.

The PP, PR, RP and RR intervals determined by the two interval measuring units 130 and 146 are then evaluated in a VT/SVT evaluation unit 150 with regard to the cause of the tachycardia. The SMART algorithm known from dual-chamber ICDs by the present applicant is preferably used here unchanged.

Figure 9:
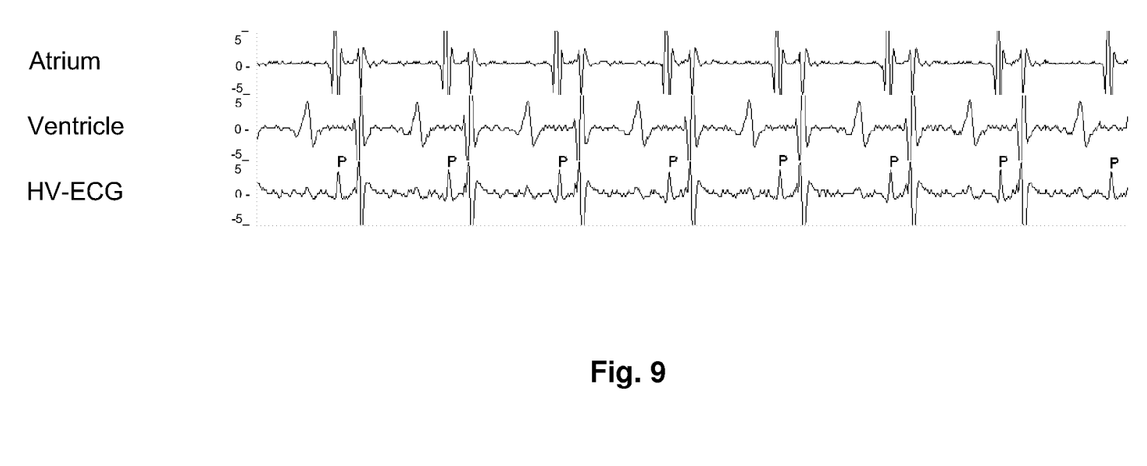
FIG. 9 shows a far-field electrocardiogram (below) obtained with the help of an implantable ventricular cardioverter/defibrillator according to FIGS. 5 through 8 together with an intraventricular electrocardiogram (center) and an intraatrial electrocardiogram (above).

FIG. 9 shows at the bottom a far-field electrocardiogram derived between the proximal shock coil and the housing of the ICD. In addition, the electrocardiograms from the right atrium (top) and the right ventricle (in the middle) are also shown. The detected P-waves are marked with a corresponding marker (P) in the far-field electrocardiogram. The illustrated intraatrial electrocardiogram cannot be recorded by the inventive heart stimulator and is shown only for illustration purposes.

What is claimed is:

1. An implantable ventricular heart stimulator (10), comprising:
   an at least partially electrically conductive housing (12);
   a terminal comprising a defibrillation electrode line terminal configured to connect a ventricular defibrillation electrode (26, 28) with a defibrillation electrode line (20) wherein said terminal is not connected to an atrial electrode line;
   a far-field electrocardiogram detection unit (70), which has a first input that is connected to the terminal for the ventricular defibrillation electrode and has a second input that is connected to the at least partially electrically conductive housing (12) and wherein the far-field electrocardiogram detection unit (70) is configured to generate a far-field electrocardiogram based on electric potentials applied to the first input and second input;
   a far-field electrocardiogram evaluation unit (72) connected to the far-field electrocardiogram detection unit (70) and wherein the far-field electrocardiogram evaluation unit (72) is configured to
   detect signal features characteristic of atrial depolarization in the far-field electrocardiogram generated by the far-field electrocardiogram detection unit (70);
   wherein said implantable ventricular heart stimulator does not comprise an atrial electrode line terminal;
   wherein the far-field electrocardiogram evaluation unit (72) is configured to detect sensing events or signal peaks in the far-field electrocardiogram which are not to be assigned to an intrinsic atrial event and to remove such signal peaks from the far-field electrocardiogram and then to further process the far-field electrocardiogram to detect atrial sensing events; and,
   wherein the implantable ventricular heart stimulator is configured as an implantable cardioverter/defibrillator and comprises a VT/SVT evaluation unit configured to make an assignment of ventricular arrhythmia to a supraventricular tachycardia or a ventricular tachycardia based on successive detected atrial events and successive ventricular events.

2. The implantable ventricular heart stimulator according to claim 1, further comprising a ventricular stimulation unit (50), which is or can be connected to a left ventricular or right ventricular stimulation electrode (22, 24) of a relatively small area in comparison with the ventricular defibrillation electrode (26, 28) and wherein the ventricular stimulation unit (50) is configured to generate and deliver ventricular stimulation pulses for stimulation of a ventricle of a heart.

3. The implantable ventricular heart stimulator according to claim 2 further comprising a stimulation control unit connected at least to the ventricular stimulation unit, wherein the far-field electrocardiogram evaluation unit (72) is configured to send atrial sensing signals that represent detected atrial events to the stimulation control unit with a time delay.

4. The implantable ventricular heart stimulator according to claim 3, wherein the implantable ventricular heart stimulator is configured as a demand heart pacemaker whose stimulation control unit inhibits delivery of the ventricular stimulation pulses if the ventricular sensing unit detects ventricular events within an AV interval, wherein the time delay corresponds to an atrial ventricular hysteresis time and the stimulation control unit is configured to start the AV interval with a delayed atrial sensing signal.

5. The implantable ventricular heart stimulator according to claim 1, further comprising a ventricular sensing unit (52), which is or can be connected to a left ventricular or right ventricular sensing electrode (22, 24) of a relatively small area in comparison with the ventricular defibrillation electrode (26, 28) and wherein the ventricular sensing unit (52) is configured to record and process electric potentials of ventricular myocardium.

6. The implantable ventricular heart stimulator according to claim 5, wherein the far-field electrocardiogram evaluation unit (72) is connected to the ventricular sensing unit (52) and is configured to assign events detected by the ventricular sensing unit (52) as ventricular events to signal peaks in the far-field electrocardiogram and to remove such signal peaks from the far-field electrocardiogram.

7. The implantable ventricular heart stimulator according to claim 1, wherein the defibrillation electrode line terminal for connection of a ventricular defibrillation electrode line is configured with two shock coils, namely one proximal shock coil (28) and one distal shock coil (26), such that the proximal and distal shock coils are connected independently of one another to the far-field electrocardiogram detection unit (70).

8. The implantable ventricular heart stimulator according to claim 1, wherein the defibrillation electrode line terminal for connection of a ventricular defibrillation electrode line is configured with two shock coils, namely one proximal shock coil and one distal shock coil, and only the proximal shock coil (28) is or can be connected to the far-field electrocardiogram detection unit (70).

9. The implantable ventricular heart stimulator according to claim 1, wherein the far-field electrocardiogram evaluation unit (72) is configured to detect sensing events in the far-field electrocardiogram by comparison with a fixed predefined or variable threshold.

10. The implantable ventricular heart stimulator according to claim 1, wherein the far-field electrocardiogram evaluation unit (72) is configured to subject the far-field electrocardiogram to a signal shape analysis to determine signal peaks which are to be assigned to ventricular events.

11. The implantable ventricular heart stimulator according to claim 1, wherein the far-field electrocardiogram evaluation unit (72) is configured to determine the signal peaks to be assigned to ventricular events in the far-field electrocardiogram based on a signal shape analysis and take into account the ventricular events detected by the ventricular sensing (52) and remove the signal peaks determined in this way from the far-field electrocardiogram and subject a remaining far-field electrocardiogram to a threshold comparison for detection of atrial events.

12. The implantable ventricular heart stimulator according to claim 1, further comprising a second terminal for a left ventricular electrode line and a stimulation control unit configured to deliver a cardiac resynchronization therapy.

13. The implantable ventricular heart stimulator according to claim 1, wherein the implantable ventricular heart stimulator is configured to detect ventricular events and to assign the ventricular events to a tachycardia as a function of a heart rate when the heart rate is above a first limit rate but below a higher second limit rate and to assign the ventricular events to a fibrillation when the heart rate is above the second limit rate, such that the implantable ventricular heart stimulator is also configured so that the far-field electrocardiogram evaluation unit detects atrial events only when the heart rate is below the second limit rate.

14. The implantable ventricular heart stimulator according to claim 1, wherein the implantable ventricular heart stimulator is configured to perform an atrial synchronous stimulation or an electrotherapy that depends on detection of atrial events if the far-field electrocardiogram evaluation unit detects atrial sensing results in the far-field electrocardiogram and otherwise switches to a single-chamber operating mode that does not rely on detection of atrial events.

15. The implantable ventricular heart stimulator according to claim 1, further comprising a digital signal processor (144) configured to perform signal processing only when measured RR intervals are within a ventricular tachycardia or VT zone of heart rate to avoid highly power consuming signal processing.

16. An implantable ventricular heart stimulator (10), comprising:
   an at least partially electrically conductive housing (12);
   a terminal comprising a defibrillation electrode line terminal configured to connect a ventricular defibrillation electrode (26, 28) with a defibrillation electrode line (20) wherein said terminal is not connected to an atrial electrode line;
   a far-field electrocardiogram detection unit (70), which has a first input that is connected to the terminal for the ventricular defibrillation electrode and has a second input that is connected to the at least partially electrically conductive housing (12) and wherein the far-field electrocardiogram detection unit (70) is configured to generate a far-field electrocardiogram based on electric potentials applied to the first input and second input;
   a far-field electrocardiogram evaluation unit (72) connected to the far-field electrocardiogram detection unit (70) and wherein the far-field electrocardiogram evaluation unit (72) is configured to
      detect signal features characteristic of atrial depolarization in the far-field electrocardiogram generated by the far-field electrocardiogram detection unit (70);
   wherein said implantable ventricular heart stimulator does not comprise an atrial electrode line terminal;
   wherein the far-field electrocardiogram evaluation unit (72) is configured to detect sensing events or signal peaks in the far-field electrocardiogram which are not to be assigned to an intrinsic atrial event through signal shape analysis to determine said signal peaks which are to be assigned to ventricular events and to remove said signal peaks from the far-field electrocardiogram and then to further process the far-field electrocardiogram to detect atrial sensing events; and,
   wherein the implantable ventricular heart stimulator is configured to detect ventricular events and to assign the ventricular events to a tachycardia as a function of a heart rate when the heart rate is above a first limit rate but below a higher second limit rate and to assign the ventricular events to a fibrillation when the heart rate is above the second limit rate, such that the implantable ventricular heart stimulator is also configured so that the far-field electrocardiogram evaluation unit detects atrial events only when the heart rate is below the second limit rate.

17. The implantable ventricular heart stimulator according to claim 16, wherein the implantable ventricular heart stimulator is configured as an implantable cardioverter/defibrillator and comprises a VT/SVT evaluation unit configured to make an assignment of ventricular arrhythmia to a supraventricular tachycardia or a ventricular tachycardia based on successive detected atrial events and successive ventricular events.

18. The implantable ventricular heart stimulator according to claim 16, wherein the implantable ventricular heart stimulator is configured to perform an atrial synchronous stimulation or an electrotherapy that depends on detection of atrial events if the far-field electrocardiogram evaluation unit detects atrial sensing results in the far-field electrocardiogram and otherwise switches to a single-chamber operating mode that does not rely on detection of atrial events.

19. The implantable ventricular heart stimulator according to claim 16, further comprising a digital signal processor (144) configured to perform signal processing only when measured RR intervals are within a ventricular tachycardia or VT zone of heart rate to avoid highly power consuming signal processing.

* * * * *